(12) United States Patent
Kyba et al.

(10) Patent No.: US 11,911,367 B2
(45) Date of Patent: Feb. 27, 2024

(54) METHODS FOR TREATING CANCER

(71) Applicant: REGENTS OF THE UNIVERSITY OF MINNESOTA, Minneapolis, MN (US)

(72) Inventors: Michael Kyba, Minneapolis, MN (US); Darko Bosnakovski, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 28 days.

(21) Appl. No.: 17/691,305

(22) Filed: Mar. 10, 2022

(65) Prior Publication Data

US 2022/0288032 A1  Sep. 15, 2022

Related U.S. Application Data

(60) Provisional application No. 63/161,255, filed on Mar. 15, 2021.

(51) Int. Cl.
*A61K 31/4184* (2006.01)
*A61P 35/00* (2006.01)

(52) U.S. Cl.
CPC .......... *A61K 31/4184* (2013.01); *A61P 35/00* (2018.01)

(58) Field of Classification Search
CPC .................................................. A61K 31/4182
USPC ....................................................... 514/387
See application file for complete search history.

(56) References Cited

U.S. PATENT DOCUMENTS

2016/0235716 A1* 8/2016 Kesicki ................ C07D 413/12

FOREIGN PATENT DOCUMENTS

WO  2016044770 A1  3/2016

OTHER PUBLICATIONS

Bhagwat, A , et al., "Targeting Transcription Factors in Cancer", Trends Cancer 1 (1), 53-65 (2015).
Bosnakovski, D , et al., "A novel P300 inhibitor reverses DUX4-mediated global histone H3 hyperacetylation, target gene expression, and cell death", Sci Adv 5, eaaw7781, 9 pages (2019).
Bosnakovski, D , et al., "An isogenetic myoblast expression screen identifies DUX4-mediated FSHD-associated molecular pathologies", EMBO J 27, 2766-2779 (2008).
Bosnakovski, D , et al., "Dux facilitates post-implantation development, but is not essential for zygotic genome activation", Biol Reprod 104, 83-93 (2021).
Bosnakovski, D , et al., "Inactivation of the CIC-DUX4 oncogene through P300/CBP inhibition, a therapeutic approach for CIC-DUX4 sarcoma", Oncogenesis 10 (68), 1-11 (2021).
Bosnakovski, D , et al., "Low level DUX4 expression disrupts myogenesis through deregulation of myogenic gene expression", Scientific Reports 8, 16957, 12 pages (2018).
Bosnakovski, D , et al., "The DUX4 homeodomains mediate inhibition of myogenesis and are functionally exchangeable with the Pax7 homeodomain", J Cell Sci 130, 3685-3697 (2017).
Chen, Z , et al., "Loss of DUX causes minor defects in zygotic genome activation and is compatible with mouse development", Nature Genetics 51, 947-951 (2019).
Choi, S , et al., "DUX4 recruits p300/CBP through its C-terminus and induces global H3K27 acetylation changes", Nucleic Acids Res 44, 5161-5173 (2016).
Choi, E , et al., "Undifferentiated Small Round Cell Sarcoma With t(4;19)(q35;q13.1) CIC-DUX4 Fusion A Novel Highly Aggressive Soft Tissue Tumor With Distinctive Histopathology", Am J Surg Pathol 37, 1379-1386 (2013).
Dixit, M , et al., "DUX4, a candidate gene of facioscapulohumeralmuscular dystrophy, encodes a transcriptionalactivator ofPITX1", Proceedings of the National Academy of Sciences of the U.S. of America 104, 18157-18162 (2007).
Donahue, J , et al., "Primary Spinal Epidural CIC-DUX4 Undifferentiated Sarcoma in a Child", Pediatr Dev Pathol 21, 411-417 (2018).
Gambarotti, M , et al., "CIC-DUX4 fusion-positive round-cell sarcomas of soft tissue and bone: a single-institution morphological and molecular analysis of seven cases", Histopathology 69, 624-634 (2016).
Graham, C , et al., "The CIC-DUX4 fusion transcript is present in a subgroup of pediatric primitive round cell sarcomas", Hum Pathol 43, 180-189 (2012).
Haidar, A , et al., "High-Grade Undifferentiated Small Round Cell Sarcoma with t(4;19)(q35;q13.1) CIC-DUX4 Fusion: Emerging Entities of Soft Tissue Tumors with Unique Histopathologic Features—A Case Report and Literature Review", Am J Case Rep 16, 87-94 (2015).
Hendrickson, P , et al., "Conserved roles of mouse DUX and human DUX4 in activating cleavage-stage genes and MERVL/HERVL retrotransposons", Nature Genetics 49, 925-934 (2017).
Hung, Y , et al., "Evaluation of ETV4 and WT1 expression in CIC-rearranged sarcomas and histologic mimics", Mod Pathol 29, 1324-1334 (2016).

(Continued)

*Primary Examiner* — Taofiq A Solola
(74) *Attorney, Agent, or Firm* — Viksnins Harris Padys Malen LLP

(57) ABSTRACT

A method for treating a cancer involving one or more translocations generating an oncogenic fusion transcription factor that requires p300/CBP for activity in an animal, comprising administering a compound of formula (I):

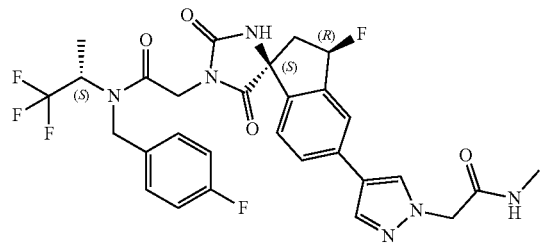

or a pharmaceutically acceptable salt thereof to the animal.

5 Claims, 13 Drawing Sheets

(56) References Cited

OTHER PUBLICATIONS

Italiano, A , et al., "High prevalence of CIC fusion with double-homeobox (DUX4) transcription factors in EWSR1-negative undifferentiated small blue round cell sarcomas", Genes Chromosomes Cancer 51, 207-218 (2012).

Kawamura-Saito, M , et al., "Fusion between CIC and DUX4 up-regulates PEA3 family genes in Ewing-like sarcomas with t(4;19)(q35;q13) translocation", Hum Mol Genet 15, 2125-2137 (2006).

Lasko, L , et al., "Discovery of a potent catalytic p300/CBP inhibitor that targets lineage-specific tumors", Nature 550 (7674), 128-132 (2017).

Le Guellec, S , et al., "ETV4 is a useful marker for the diagnosis of CIC-rearranged undifferentiated round-cell sarcomas: a study of 127 cases including mimicking lesions", Mod Pathol 29, 1523-1531 (2016).

Lemmers, R , et al., "A unifying genetic model for facioscapulohumeral muscular dystrophy", Science 329, 1650-1653 (2010).

Mertens, F , et al., "Gene fusions in soft tissue tumors: Recurrent and overlapping pathogenetic themes", Genes Chromosomes Cancer 55 (4), 291-310 (2016).

Okimoto, R , et al., "CIC-DUX4 oncoprotein drives sarcoma metastasis and tumorigenesis via distinct regulatory programs", J Clin Invest 129 (8), 3401-3406 (2019).

Ricker, C , et al., "Undifferentiated small round cell sarcoma in a young male: a case report", Cold Spring Harb Mol Case Stud 6 (1), a004812, 22 pages (2020).

Yoshida, A , et al., "CIC-rearranged Sarcomas, A Study of 20 Cases and Comparisons With Ewing Sarcomas", Am J Surg Pathol 40, 313-323 (2016).

* cited by examiner

A

B

METHODS FOR TREATING CANCER

CROSS-REFERENCE TO RELATED APPLICATION

This application claims priority to U.S. Provisional Application No. 63/161,255 that was filed on Mar. 15, 2021. The entire content of the applications referenced above is hereby incorporated by reference herein.

STATEMENT REGARDING FEDERALLY SPONSORED RESEARCH

This invention was made with government support under AR055685 awarded by the National Institutes of Health. The government has certain rights in the invention.

BACKGROUND

The biological regulation of transcription factors and repressor proteins is an essential mechanism for maintaining cellular homeostasis and is often dysregulated in human cancer (Bhagwat A S., et al. *Trends Cancer.* 2015; 1(1):53-65). Chromosomal rearrangements involving transcriptional regulatory genes that lead to transcriptional dysregulation are present in many cancers, including approximately 30% of all soft tissue sarcomas (Mertens F, et al. *Genes Chromosomes Cancer.* 2016; 55(4):291-310).

A newly recognized commonly pediatric subtype of undifferentiated round cell sarcoma that is driven by fusion between the cell cycle regulator and transcriptional repressor, capicua (CIC), and the transcriptional activator, DUX4, has been identified based on its histology, clinical differences, and aggressiveness (Italiano, A. et al. *Genes Chromosomes Cancer* 51, 207-218 (2012); Hung, Y. P., Fletcher, C. D. & Hornick, J. L. *Mod Pathol* 29, 1324-1334 (2016); Gambarotti. M. et al. *Histopaihology* 69, 624-634 (2016); Donahue, J. E. et al. *Pediatr Dev Pathol* 21, 411-417 (2018); Ricker, C. A. et al. *Cold Spring Harb Mol Case Stud* 6 (2020); Choi, E. Y. et al. *Am J Surg Pathol* 37, 1379-1386 (2013); Graham, C., et al., Hum Pathol 43, 180-189 (2012); and Kawamura-Saito, M. et al. *Hum Mol Genet* 15, 2125-2137 (2006)).

CIC-DUX4 sarcoma (CDS) occurs predominantly in children and young adults and usually develops in somatic soft tissues (Donahue, J. E. et al. *Pediatr Der Pathol* 21, 411-417 (2018); Ricker, C. A. et al. *Cold Spring Harb Mol Case Stud* 6 (2020); Yoshida, A. et al. *Am J Surg Pathol* 40, 313-323 (2016); and Le Guellec, S. et al., *Mod Pathol* 29, 1523-1531 (2016)). Patients with CDS show an aggressive clinical course with a high metastatic rate and quickly develop resistance to chemotherapy. The median survival is less than 2 years (Choi, E. Y. et al. *Am J Surg Pathol* 37, 1379-1386 (2013); Yoshida, A. et al. *Am J Surg Pathol* 40, 313-323 (2016); and Haidar, A., Arekapudi, et al., *Am J Case Rep* 16, 87-94 (2015)). CDS at the molecular level is poorly understood and so far, all of the treatment efforts have poor and unsatisfactory outcomes.

The CIC-DUX4 fusion is the product of a translocation between the Capicua Transcriptional Repressor (CIC) on chromosome 19 and DUX4 on chromosome 4 (4;19)(q35; q13), or on rare occasions with DUX4 from chromosome 10 (10;19)(q26;q13). The CIC-DUX4 oncoprotein contains the majority of the N-terminal part of CIC, which encompasses its DNA binding domain, and a small C-terminal part of DLX4 that has strong transcriptional activation properties (Kawamura-Saito, M. et al. Hum Mo Genet 15, 2$^1$25-2137 (2006); Bosnakovski, D. et al. *J Cell Sci* 130, 3685-3697 (2017); and Choi, S. H. et al., *Nucleic Acids Res* 44, 5161-5173 (2016)). The acquisition of the DUX4 C-terminus transforms CIC from a transcriptional repressor into an activator. Crucial cell cycle genes, as well as genes involved in driving metastasis previously repressed by CIC, are expressed at high levels, driving uncontrolled cell division and malignant transformation (Kawamura-Saito, M. et al. *Hum Mol Genet* 15, 2125-2137 (2006); and Okimoto. R. A. et al., *J Clin Invest* 129, 3401-3406 (2019)).

DUX4 is a transcription factor involved in early embryogenesis and facioscapulohumeral muscular dystrophy (FSHD) (Hendrickson, P. G. et al., *Nature genetics* 49, 925-934 (2017); Chen, Z. & Zhang, Y. *Nature genetics* 51, 947-951 (2019); Bosnakovski, D., et al., *Biol Reprod* 104, 83-93 (2021); Lemmers, R. J. et al., *Science* 329, 1650-1653 (2010); Bosnakovski, D. et al., *EMBO J* 27, 2766-2779 (2008); Dixit, M. et al., *Proceedings of the National Academy of Sciences of the United States of America* 104, 18157-18162 (2007)). The C-terminus of DUX4 recruits p300/CBP and induces both local histone (H3) acetylation and total nuclear histone H3 hyperacetylation (Choi, S. H. et al., *Nucleic Acids Res* 44, 5161-5173 (2016)). Deletion of the C-terminus of DUX4 eliminates induced H3 acetylation and target gene expression (Bosnakovski, D. et al. J Cell Sci 130, 3685-3697 (2017); Choi, S. H. et al., *Nucleic Acids Res* 44, 5161-5173 (2016); and Bosnakovski, D. et al., *Scientific reports* 8, 16957 (2018)). Similar effects were achieved by specific p300 inhibition in cells expressing DUX4 (Bosnakovski, D. et al., *Sci Adv* 5, eaaw7781 (2019)).

Currently, there is a need for effective therapies for suppressing CIC-DUX4-induced cytotoxicity. There is also a need for compounds that are useful for treating cancers involving one or more translocations generating an oncogenic fusion transcription factor that requires p300/CBP for activity, such as, for example, a cancer involving the CIC-DUX4 fusion protein, like a sarcoma or a pediatric sarcoma.

SUMMARY

Because CIC-DUX4 acquires the p300-interacting activation domain of DUX4, it was hypothesized that its transcriptional activation potential, and thus the oncogenicity of CIC-DUX4, might require p300 or its homologue, CBP. Recently, a new class of histone acetyltransferase inhibitor with high selectivity for p300 and CBP has been described, and two compounds. A-485, and iP300w, have been shown to inhibit acetylation by p300 and CBP both in vitro and in vivo, with iP300w having the ability to reverse gene expression changes caused by DUX4 (Bosnakovski, D. et al., *Sci Adv* 5, eaaw7781 (2019); and Lasko, L. M. et al., *Nature* 550, 128-132 (2017)). Based on the above hypothesis, iP300w might possibly counteract the CIC-DUX4 gene expression program and might be a particularly effective therapy for CDS.

Applicant has demonstrated that CIC-DUX4 requires p300/CBP for its activity and that CIC-DUX4 induces a global increase in H3 acetylation, like DUX4, which is reversible with iP300w treatment. Additionally, it has been found that CIC-DUX4 activity is potently blocked by iP300w, and that this compound has potent activity against CDS cell lines in vitro, and in an in vivo cancer xenograft assay.

Accordingly, in one aspect the present invention provides a method for treating a cancer involving one or more translocations generating an oncogenic fusion transcription factor that requires p300/CBP for activity in an animal, comprising administering a compound of formula (1):

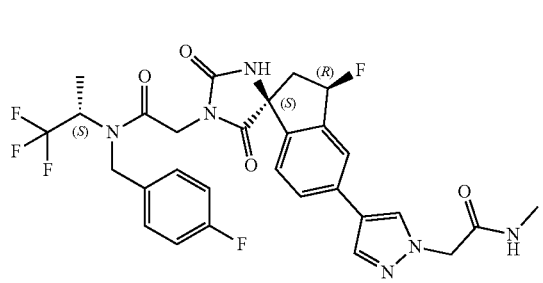

(I)

or a pharmaceutically acceptable salt thereof to the animal. The compound of Formula (I) is also known as iP300w.

In another aspect, the present invention provides a compound of formula (I):

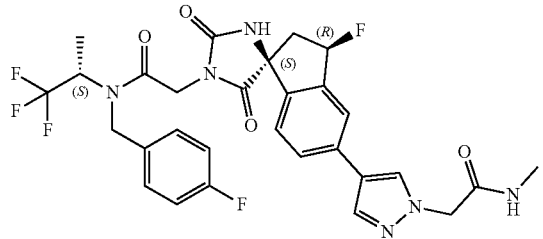

(I)

or a pharmaceutically acceptable salt thereof for the treatment of a cancer involving one or more translocations generating an oncogenic fusion transcription factor that requires p300/CBP for activity.

In another aspect, the present invention provides a pharmaceutical composition comprising compound of formula (I):

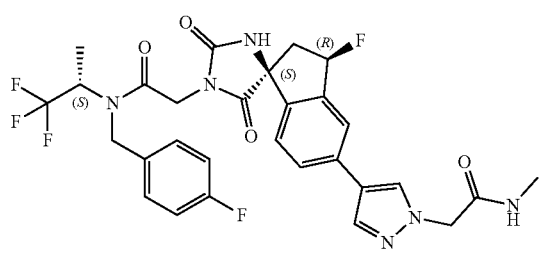

(I)

or a pharmaceutically acceptable salt thereof and a second therapeutic agent useful for treating a cancer involving one or more translocations generating an oncogenic fusion transcription factor that requires p300/CBP for activity.

In one aspect the resent invention provides the use of a compound of formula (I):

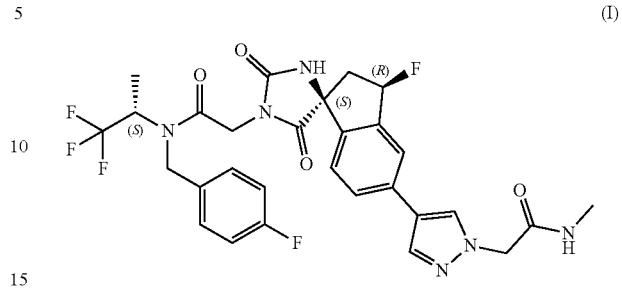

(I)

or a pharmaceutically acceptable salt thereof for the manufacture of a medicament for treating a cancer involving one or more translocations generating an oncogenic fusion transcription factor that requires p300/CBP for activity.

BRIEF DESCRIPTION OF DRAWINGS

(FIG. 1A) Western blots for p300 and CBP in NCC-CDS-X1 cells after 96 hours transfection with siRNAs for P300 and CBP. (FIG. 1B) ATP assay for cell viability of NCC-CDS-X1 at 72 hours and 96 hours post-transfection with p300 and/or CBP siRNA. Non-treated cells and cells transfected with non-targeting siRNA (scramble) were used as negative controls. (FIG. 1C) ATP assay in Kitra-SRS cell line in the same experimental conditions as explained in "A". Data are presented as mean±SEM; ****$p<0.0001$, by two-way ANOVA. Results are presented as relative expression to control (n=4). (FIG. 1D) RT-qPCR for p300. CBP, and CIC-DUX4 target genes in NCC-CDS-X1. Analyses were performed 48 hours post-transfection with p300 and/or CBP siRNA. Data are presented as mean±SEM; *$p<0.05$, $p<0.01$, *$p<0.001$ by one-way ANOVA. Results are presented as relative expression to control (n=3).

(FIG. 2A) ATP assay at 48 hours and 96 hours of treatment of NCC-CDS-X1 cells with different concentrations of iP300w stereoisomers and A-485. (FIG. 2B) $IC_{50}$ values of A485, iP300v and iP300w in NCC-CDS-X1 cells at 48 and 98 hours of treatment. (FIG. 2C) RT-qPCR for CIC-DUX4 target genes in NCC-CDS-X1 cells after 24 hours treatment with 0.03 μM and 0.3 μM iP300w stereoisomers and A-485. Data is presented as mean±SEM; *$p<0.05$, by two-way ANOVA. Results are presented as relative expression to control (n=3).

(FIG. 3A) Morphology of NCC-CDS-X1 and Kitra-SRS cell cultures at 48 hours of treatment with iP300w (0.3 μM). (FIG. 3B) ATP assay for cell viability at 48 hours of treatment with a serial dilution of iP300w. (FIG. 3C) NCC-CDS-X1 spheres morphology after 4 days of treatment with iP300w (0.3 μM). (FIG. 3D) Immunofluorescence for Ki-67 in NCC-CDS-X1 and Kitra-SRS cells treated for 24 hours with iP300w (0.3 μM). (FIG. 3E) Representative FACS analyses for EdU incorporation in NCC-CDS-X1 cells. Cells were treated with 0.3 μM iP300w for 4, 24, 48, and 72 hours. In the last 4 hours of treatment proliferating cells were labeled with EdU (10 μM). (FIG. 3F) Summary of the FACS analyses presented in "E". Data are presented as mean±SEM; *$p<0.05$, by one-way ANOVA. Results are presented as relative expression to control (n=3).

(FIG. 3G) Representative FACS analyses for EdU incorporation in NCC-CDS-X1 cells after pulse of iP300w (0.3 µM). Cells were incubated for 4 or 24 hours with iP300w (0.3 µM) and FACS analyzed 24 hours later. In the last 4 hours of the experiment, the cells were incubated with EdU. (FIG. 3H) Summary of FACS analyses presented in "F". (FIG. 3I) ATP assay for cell viability in NCC-CDS-X1 and in 3 different Ewing sarcoma cell lines (AF573, TC71, A673). Cells were treated with 0.003 and 0.03 µM for 48 hours. Data is presented as mean±SEM; n=4. (FIG. 3J) Size of the NCC-CDS-X1 xenograft tumors in control and treated mice over 12 days. Mice were treated 1.4 mg/kg iP300w twice daily. (FIG. 3K) Gross morphology of dissected tumors at the endpoint of the experiment (day 12) presented in "1".

(FIG. 4A) Scatter plots of −log 10 fold change of the Benjamini-Hochberg adjusted p-value versus the observed log 2 fold change in gene expression. The changes with 4 hours and 24 hours of iP300w treatment are shown on the left and right respectively. The y-axis in each plot has been expanded in the lower panels relative to the upper panels. (FIG. 4B) Heatmap of the log 2 padded FPKM values of CIC-DUX4 targets from Okimoto et al. in NCC-CDS1-X1 cells upon treatment with iP300w. (FIG. 4C) Enriched KEGG pathways (hypergeometric test, Benjamini-Hochberg adjusted p-value<0.05) of the differentially expressed genes at 4 hours (left) and 24 hours (lower right). The x-axis corresponds to the log 10 adjusted p-value such that down regulated genes are shown on the negative axis (blue) and up regulated genes (orange) are shown on the positive axis in each plot.

(FIG. 5A) Immunostaining for CIC-DUX4 in 3T3-CIC-DUX4 cell line. (FIG. 5B) RT-qPCR for CIC-DUX4 and its target genes in 3T3-CIC-DUX4 cell line treated for 18 hours with iP300w. (FIG. 5C) Western blot analyses for ETV4 and acetylated H3K18 and H3K27 in 3T3-CIC-DUX4 cell line treated for 18 hours with iP300w. (FIG. 5D) Western blot analyses for H3 acetylation markers in CIC-DUX4 sarcoma cell lines treated for 18 hours with iP300w.

(FIG. 7A) at 48 hours. (FIG. 7B) at 98 hours.

(FIG. 10A) ATP assay for cell viability on Panc1, MiaPaca2, CFPac1 pancreatic cancer cells treated with serial of iP300w dilutions for 48 hours. (FIG. 10B) ATP assay for cell viability on HTC116, MKN28, KATO3 colorectal cancer cells treated with serial of iP300w dilutions for 48 hours. (FIG. 10C) ATP assay on LCHN-Myoblast treated for 48 and 74 hours with iP300w. Data are presented as mean±SEM; *p<0.001, **p<0.0001 by one-way ANOVA, n=4.

(FIG. 11A) Enriched KEGG pathways (hypergeometric test, Benjamini-Hochberg adjusted p-value<0.05) of the downregulated genes at 4 hours (gray) and 24 hours (black) that have previously been identified as CIC-DUX4 targets. (FIG. 11B) Barplots of log 2 transformed FPKM values for genes in enriched KEGG pathways in (A) for the control (white), 4 hours (gray) and 24 hours (black) conditions.

(FIG. 12A) RT-qPCR for CIC-DUX4 target genes in C2C12-CIC-DUX4 mouse myoblasts treated with 0.3 µM iP300w for 18 hours. (FIG. 12B) RT-qPCR for CIC-DUX4 target genes in LHCN-CIC-DUX4 human myoblasts treated with 0.3 µM iP300w for 18 hours. (FIG. 12C) Western blots for acetylated H3K18 and H3K27 in the conditions presented in A and B, above.

DETAILED DESCRIPTION

Figures 1A, 1B, 1C, 1D:
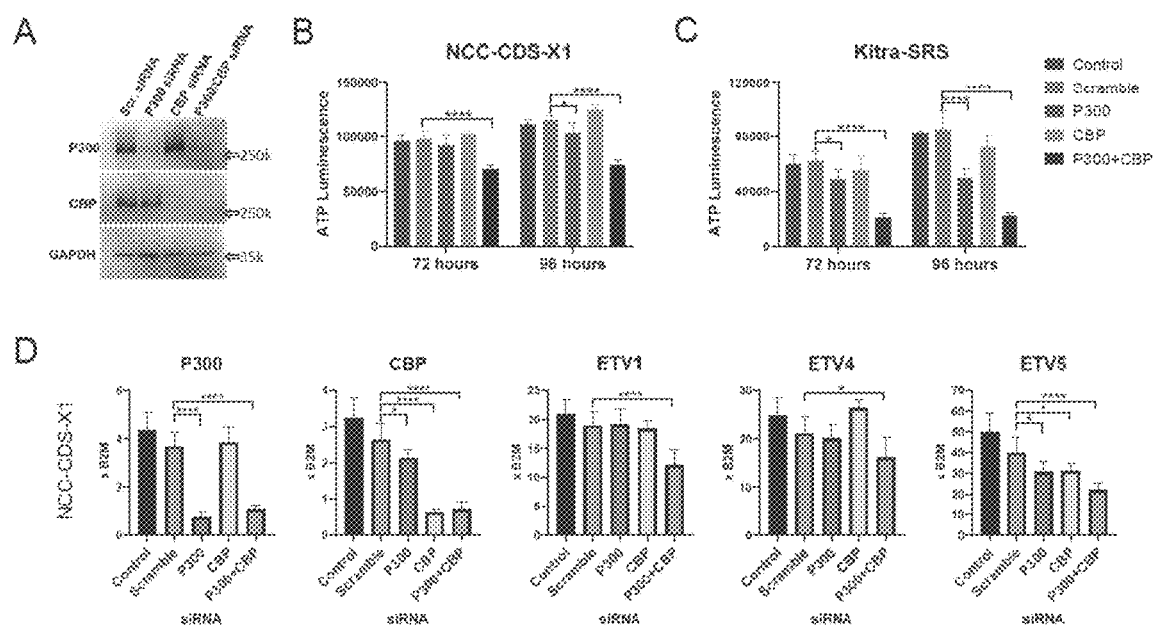
FIGS. 1A-1D. p300/CBP is required for CIC-DUX4 activity.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention.

The term "animal" as used herein includes mammals such as humans, higher non-human primates, rodents, domestic, cows, horses, pigs, sheep, dogs and cats. In one embodiment, the animal is a mammal. In one embodiment the animal is a human.

The term p300 refers to the protein, "E1A binding protein p300", Gene ID: 2033; and the term CBP refers to the protein. "CREB Binding Protein", Gene ID: 1387.

Some, but not all, oncogenic fusion transcription factors require p300/CBP for their activity. Not all proteins that interact with p300 are inhibited by the compound of formula (I). Transcription factors can interact with multiple cofactors; p300 could be sufficient but not necessary, even in a case where a transcription factor has been shown to interact directly with p300. Cancers involving a translocation generating an oncogenic fusion protein transcription factor that require p300/CBP for their activity can be identified using standard techniques, for example, by removing p300 (and CBP, its homologue) by knockout, knockdown, or small molecule inhibition.

DUX4 (Double Homeobox Chromosome 4) is a transcription factor encoded by the D4Z4 macrosatellite repeat sequence. The D4Z4 sequence encoding DUX4 is present in subtelomeric region of chromosomes 4 q and 10 q in long tandem arrays, as well as at other places in the human genome.

Fusion transcription factors in which one part is a transcription factor that has been shown to use p300 include AML-ETO, ATXN1-DUX4, CIC-FOXO4, CIC-NUTM1, MYB-NFIB, RUNX1-ETO, PAX3-FOXO1, PAX3-FOXO4, PAX3-INO80D, EWSR1-FLI1, PAX3-AFX, PAX3-NCOA1, PAX3-NCOA2, PAX7-FOXO1, ASPSCR1-TFE3, EWSR1-CREB1, EWSR1-ATF1, PAX3-MAML3, MECT1-MAML2, BRD4-NUTM1, BRD3-NUTM1, NSD3-NUTM1, YWHAE-NUTM2, EWSR1-WT1, EP300-BCOR, FUS-ERG, FUS-CREB3L1. FUS-CREB3L2a, EWSR1-CREB1, EWSR1-CREB3L1, EWSR1-CREB3L2, FUS-CREB3L2, FUS-DDIT3a, NAB2-STAT6, VGLL2-CITED2, SS18-SSX1, SS18-SSX2, SS18-SSX4, SS18L1-SSX1, BCOR-MAML3, NUTM2A-CIC, YWHAE-NUTM2B, EWSR1-SP3, PAX8-PPARG, RUNX1-ET, TMPRSS2-ERG, TMPRSS2-ETV1, and TMPRSS2-ETV4.

RUNX1-ETO and PAX3-FOXO1 are oncogenic fusion transcription factors generated by chromosomal translocations, similar to the way CIC-DUX4 is generated. They cause leukemia (RUNX1-ETO) or rhabdomyosarcoma (PAX3-FOXO1).

The term "CIC-DUX4" refers to the capicua-double homeobox 4 fusion protein, which is a transcription factor that is generated by fusion of the CIC gene with that of DUX4. This is commonly due to translocation of chromosomes 4 and 19 t(4;19), or of chromosomes 10 and 19 t(10,19), as DUX4 is a repeated gene, present on both chromosome 4 and 10, as well as at other sites in the genome. The CIC-DUX4 fusion protein defines certain undifferentiated round cell sarcomas with high metastatic propensity and poor clinical outcomes.

In one embodiment, the cancer is a sarcoma that involves CIC-DUX4 fusion. In another embodiment, the cancer is a pediatric sarcoma.

The pharmaceutical compositions of the invention can comprise one or more excipients. When used in combination with the pharmaceutical compositions of the invention the term "excipients" refers generally to an additional ingredient that is combined with the compound of formula (1) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compound of formula I can be formulated as A pharmaceutical composition and administered to an animal, such as a human patient, in a variety of forms adapted to the chosen route of administration, i.e., orally or parenterally, by intravenous, intramuscular, topical or subcutaneous routes.

Thus, the compound may be systemically administered, e.g., orally, in combination with a pharmaceutically acceptable vehicle such as an inert diluent or an assimilable edible carrier. The compound may be enclosed in hard- or soft-shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or using surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful dosages of the compound of formula I can be determined by comparing it's in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

The compound of Formula (I) (also known as iP300w) can be prepared as described in International Patent Application Publication Number WO2016/044770. iP300w is also commercially available from Tocris Bioscience.

The invention will now be illustrated by the following non-limiting Examples.

EXAMPLES

Example 1. Biological Evaluation

Methods
Cell Culture.

Basal media were purchased from HyClone, fetal bovine serum (FBS) was from PeakSerum (Ps-FB3, lot 293Q16), and Glutamax (Glu) and Penicillin/Streptomycin (P/S) were from GIBCO. NCC-CDS-X1 (CIC-DUX4 sarcoma cell line, a generous gift from Tadashi Kondo) cell line was cultured in RPMI with 10% FBS, Glu and P/S, Kitra-SRS (CIC-DUX4 sarcoma cell line, a generous gift from Hidetatsu Otani), 3T3, 293T and C2C12 cell lines were cultured in DMEM/10% FBS/Glu/P/S. The immortalized human myoblast LHCN-M2 cell line was cultured in proliferation medium: F10 supplemented with 20% FBS, 2-mercaptoethanol 1X (GIBCO), $10^{-9}$ M dexamethasone (Sigma), 10 ng/mL bFGF (Peprotech), and Glu/P/S. All cells were cultured at 37° C. in a 5% $CO_2$ atmosphere.

Antibodies, Western Blot, and Immunofluorescence.

For western blot analyses, cells were lysed with RIPA buffer supplemented with protease inhibitor cocktail (Complete. Roche), and proteins were separated on 10% SDS-PAGE gels, then transferred to PVDF membranes. Antibodies were diluted in 5% skim milk in TBST and incubated overnight at 4° C. or 1 hour at RT. An appropriate secondary HRP conjugated antibody was incubated for 1 hour at RT. Membranes were then washed with TBST, and signal was visualized using Pierce ECL western blotting substrate (Thermo Scientific). For immunofluorescence, cells cultured in 96 well plates were fixed in 4% PFA for 10 min., washed twice with PBS, permeabilized with 0.3% Triton X for 30 min, and blocked with 3% BSA for 1 hour at R/T. Primary antibodies were diluted in 3% BSA and incubated o/n at 4° C. An appropriate conjugated secondary antibody was applied for 60 min at RT. Nuclei were visualized using DAPI (1:5000, Sigma). Antibodies used in the study: GAPDH-HRP (1:5000, 60004, Proteintech), rabbit anti-Histone H3K18Ac (1:500, ab1191, Abcam), rabbit anti-Histone H3K27Ac (1:500, ab1791, Abcam, lot: GR3297878-1), rabbit anti-ETV4 (1:250, D2720, Santa Cruz), rabbit anti-Ki-67 (dilution 1:250, 9129T, Cell Signaling, lot: 3), rabbit anti-DUX4 (1:1000, ab124699, Abcam), secondary Alexa fluor 555 Goat Anti-Rabbit (1:500, Invitrogen), anti-rabbit CBP (1:1000, 7389S, Cell Signaling, lot: 5), anti-mouse p300 (1:500, 61401, Active Motif, lot #31420004), HRP conjugated anti-rabbit (1:5000, 111-035-003, Jackson Immuno Research, lot: 149393), and HRP conjugated anti-mouse: (1:2500, NBPI-75130, Novus, lot 58-173-090418).

Cell Viability (ATP) Assay.

Cell lines were plated in a 96 well dish ($1\times10^5$ cells/well), and the following day were treated with iP300w or its stereoisomers. ATP assays were performed using CellTiter-Glo® Luminescent Cell Viability Assay (Promega) according to the manufacturer's instructions. Luminescence was analyzed on POLARstar Optima Microplate Reader (BMG Labtech, Offenburg, Germany).

Spheroid Assay.

For spheroid formation assays, $2.5\times10^4$ NCC-CDS-X1 cells were seeded into 96-well plates (96-Well Clear Flat Bottom Ultra-Low Attachment Microplate; Corning, Inc., Corning, NY, USA) in MEM/10% FBS media. Treatment with iP300w was started two days after the plating when the cells formed compact spheres.

EdU Incorporation.

EdU labeling and visualization was done using Click-iT® EdU Flow Cytometry Assay Kit (Thermo Fisher Scientific). Briefly, $1\times10^5$ NCC-CDS-X1 cells were plated in each well of a 24-well plate. The following day, continual treatment with 0.3 µM iP300w was initiated. For the pulse experiment, cells were treated with iP300w for 4 or 24 hours and analyzed 24 hours later. Cells were cultured with EdU (10 nM) in the last 4 hours of the experiment, and samples were prepared for analyses according to the manufacture's instruction. FACS analyses were performed on a BD FACSAria instrument and data was analyzed using FlowJo (BD Biosciences). Experiments were performed on at least three biological replicates.

Mouse Tumor Formation and Evaluation of iP300w In Vivo.

Mice were maintained, and in vivo experiments were conducted at the University of Minnesota Research Animal Resources facility, under a protocol (1903-36866A) approved by IACUC. Immunodeficient NSG-MDX mice (n=8) were transplanted with $1\times10^7$ NCC-CDS-X1 cells resuspended in 100 uL of a mixture of medium and Matrigel (Corning). Visible tumor masses at the sites of injection were detected on day 9 after transplantation. All the injected mice developed tumors. At this point, the mice were randomized into two groups, control and iP300w treated, and initial measurement of the tumors was performed, iP300w was initially dissolved in DMSO at 10 mM and then diluted in 100 μL PBS. Each mouse received 1.4 mg/kg iP300w intraperitoneally twice daily or vehicle in the control group. Tumor size was recorded every 4 days and the volume was calculated using the formula (length×width$^2$)/2.

Generation of CIC-DUX4 Expression Cell Lines.

Viral supernatants were produced in 293T cells. For transducing mouse cells (3T3 and C2C12), the CIC-DUX4 expression vector was packed with pCL-Eco, and for infecting human cells (293T, LHCN-M2) with psPAX2 and pMD2.G using FUGENE 6 (Roche). Viral supernatant was collected at 48 hours and 72 hours post-transfection and applied to the cells. Two days post-infection GFP positive cells were sorted using a BD FACSAria II. Established cell lines were tested for CIC-DUX4 expression by immuno-fluorescence and RT-qPCR.

RNA Isolation, Quantitative Real-Time RT-PCR (RT-qPCR), and RNAseq.

RNA was extracted using an RNA extraction kit (Zymo) and cDNA was made using 0.5 μg total RNA with oligo-dT primer and Verso cDNA Synthesis Kit (Thermo Scientific) following the manufacturer's instructions. qPCRs were performed by using Premix Ex Taq (Probe qPCR. Takara) or SYBR-green. Gene expression levels were normalized to that of GAPDH and nalyzed with 7500 System Software using the ΔCT method (Applied Biosystems). RNA-seq library preparation was done with 500 ng total RNA from NCC-CDS-X1 cells treated for 4 or 24 hours with iP300w (0.3 μM) using the Swift Rapid RNA Library Kit (Swift-Bioscience). 36 base paired-end sequencing was performed on an Illumina NextSeq instrument at the University of Minnesota Genomics Center.

RNA Interference.

NCC-CDS-X1 and Kitra-SRS cells were seeded into 96-well plates (5×10$^4$/well) for cell viability evaluation or a 24-well plate (1.5×10$^5$/well) for RNA isolation. The following day, 50 nM siRNA for human p300 (L-003486-00-0005), CREBBP (L-003477-00-0005), or scrambled control (all from Dharmacon) were transfected using Lipofectamine RNAiMAX (Invitrogen). RNA was isolated 48 hours post-transfection and the effect on cell viability was analyzed at 72 hours and 96 hours post-transfection.

Bioinformatics.

Paired-end Illumina sequencing reads were trimmed with TrimGalore (0.6.0) and transcript abundance was quantified using the human Gencode annotations (v34) using Salmon (v 1.2.1) with the GC-bias correction option. Counts were imported into R (v 4.0.2) using tximeta (v 1.6.3). Differentially expressed genes were identified with DESeq2 (v 1.28.1) and figures were made with the ComplexHeatmap (v 2.4.3), clusterProfiler (v 3.16.1) and ggplot2 (v 3.3.2) R packages. Sequencing reads and processed data have been deposited into GEO under the accession number GSE165729.

Statistics. Graphpad Prism software was used for statistical analyses of the data, except when indicated. Differences between groups were evaluated by one-way or two-way analysis of variance (ANOVA) followed by Tukey's post hoc tests. Differences were considered significant at p-values of 0.05 or lower.

CIC-DUX4 Acts Through p300/CBP

The C-terminus of DUX4 interacts with p300 and induces both DUX4 target locus-specific acetylation as well as a global elevation of acetylation on H3K18 and HK27 (Choi, S. H. et al., Nucleic Acids Res 44, 5161-5173 (2016); and Bosnakovski, D. et al., Sci Adv 5, eaaw7781 (2019)). Thus, it is possible that CIC-DUX4 also requires p300/CBP for activation of its targets. To test this hypothesis, p300 and CBP were knocked down in two cell lines, NCC-CDS-X1 and KITRA-SRS, derived from independent CDS tumors (Nakai, S. et al., Scientific reports 9, 15812 (2019); and Oyama, R. et al., Scientific reports 7, 4712 (2017)) and evaluated cell viability and CIC-DUX4 target gene expression in these cells. The efficiency of the knockdown was confirmed by western blot (FIG. 1A).

Figure 7A:
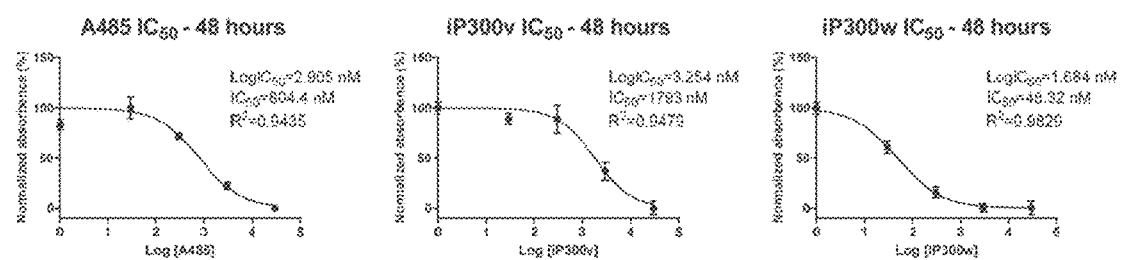
FIGS. 7A-7B. Individual $IC_{50}$ values for A485, iP300v and iP300w in NCC-CDS-X1 cells.
Figure 7B:
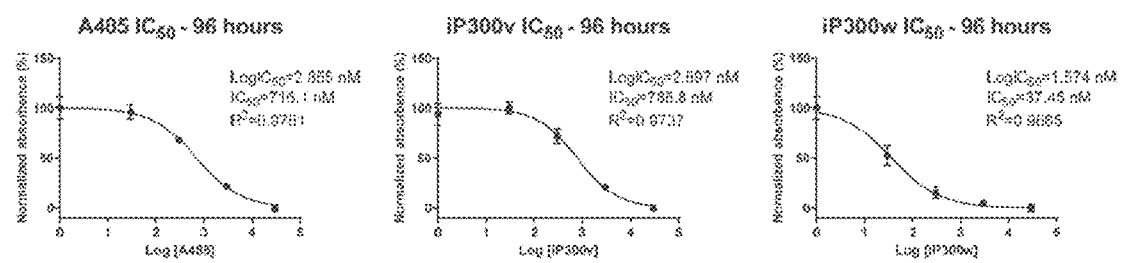

Co-transfection with p300 and CBP siRNA resulted in significant reductions of cell viability in both cell lines at 72 hours and 96 hours post-transfection (FIG. 1B, C). Notably, a slight but still significant decrease in cell proliferation was detected in the cells in which only p300 was targeted. The knockdown also resulted in reductions of the key CIC-DUX4 target genes, ETV1, 4, and 5 (FIG. 1D, FIG. 7). ETV4 is a well-established CIC-DUX4 target and cancer metastatic driver that has been used to distinguish CDS from the other Ewing sarcomas (Kawamura-Saito, M. et al. Hum Mol Genet 15, 2125-2137 (2006); Le Guellec. S. et al., Mod Pathol 29, 1523-1531 (2016); Okimoto, R. A. et al., J Cin Invest 129, 3401-3406 (2019); and Specht. K. et al., Genes Chromosomes Cancer 53, 622-633 (2014)). Thus, CIC-DUX4 transcriptional activity and with it, CDS proliferation and/or survival, depends on p300/CBP.

iP300w, a Potent p300/CBP Inhibitor

Figures 3A, 3B, 3C, 3D:
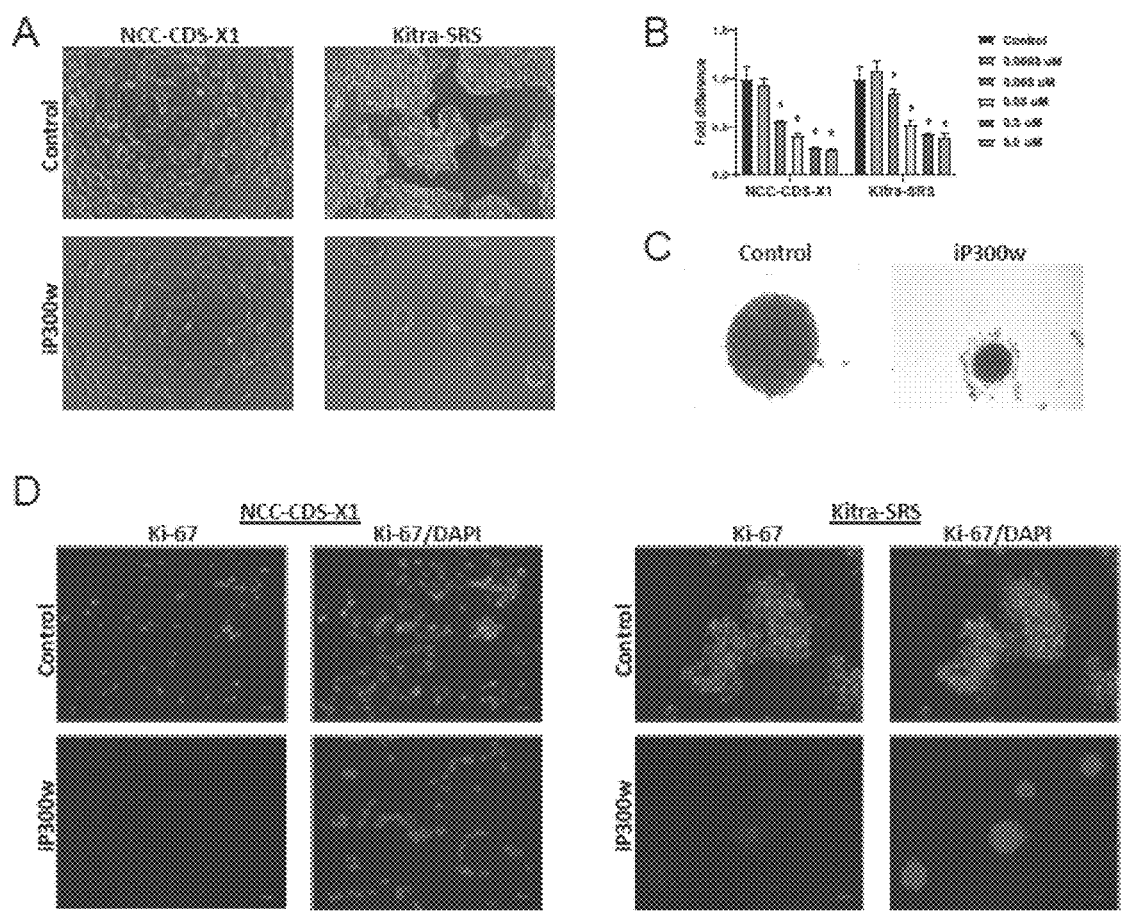
FIGS. 3A-3K. iP300w suppresses CIC-DUX2 sarcoma cell proliferation In vivo and in vitro.
Figures 3E, 3F, 3G, 3H, 3I, 3J, 3K:
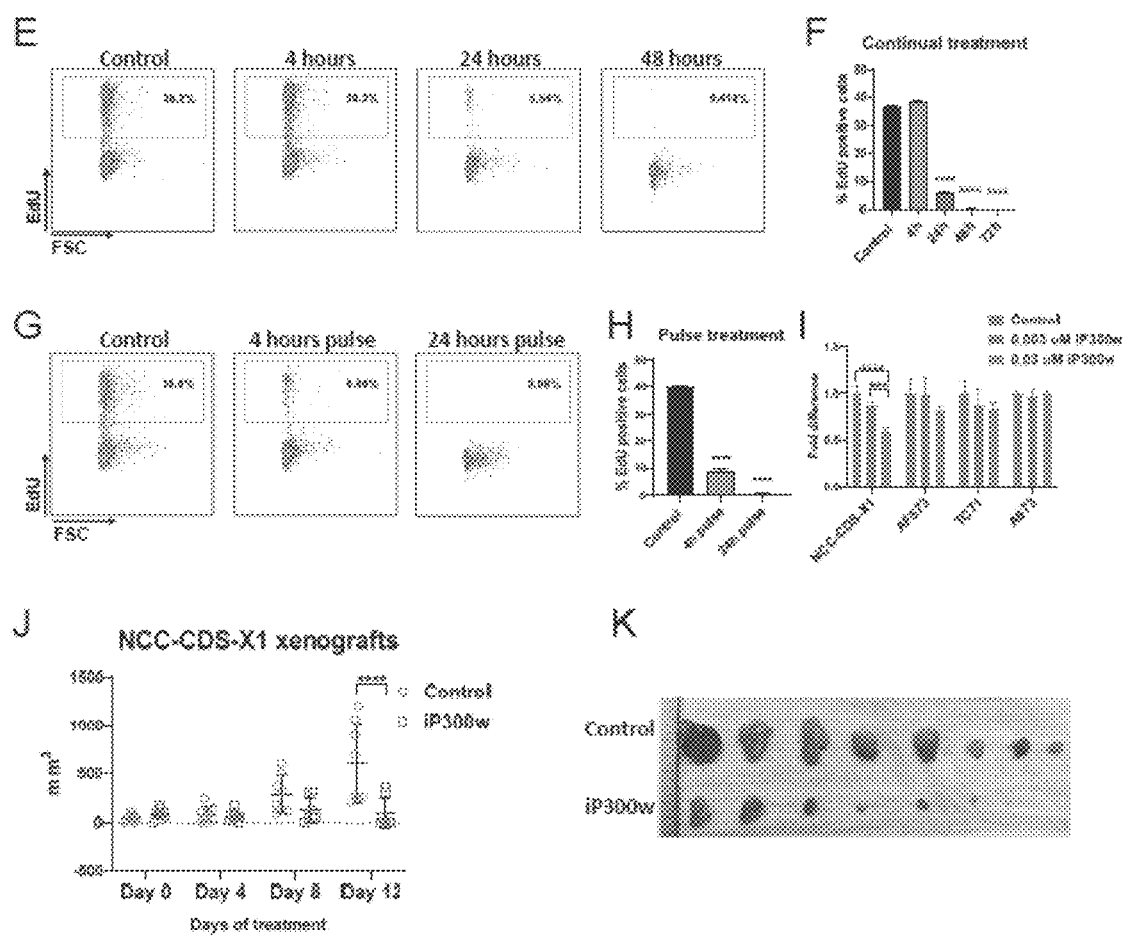

The first potent and highly selective inhibitor of the HAT domain of p300 and CBP to be reported was A-485 (FIG. 3A; Lasko, L. M. et al., Nature 550, 128-132 (2017) a competitive binder for the acetyl co-A site of p300. Several structurally related compounds from the same series have recently been described to have p300 inhibitory activity (Bosnakovski, D. et al., Sci Adv 5, eaaw7781 (2019); Michaelides, M. R. et al., ACS Med Chem Lett 9, 28-33 (2018); Wilson, J. E. et al., ACS Med Chem Lett 11, 1324-1329 (2020); and Yang, Y. et al., J Med Chem 63, 1337-1360 (2020)). One of these, iP300, was shown to have activity residing in a single diastereomer with undefined stereochemistry, named 'iP300w' (Bosnakovski, D. et al., Sci Adv 5, eaaw7781 (2019)). A second undefined diastereomer ('iP300v') exhibited substantially reduced activity (Bosnakovski, D. et al., Sci Adv 5, eaaw7781 (2019)). The structures for iP300w and A-485 are shown below.

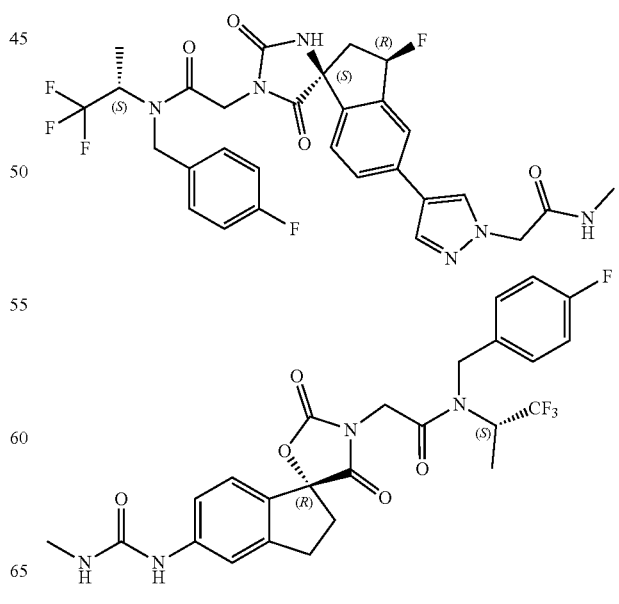

iP300w and Related Compounds Decrease CIC-DUX4 Sarcoma Cell Viability

Figures 2A, 2B, 2C:
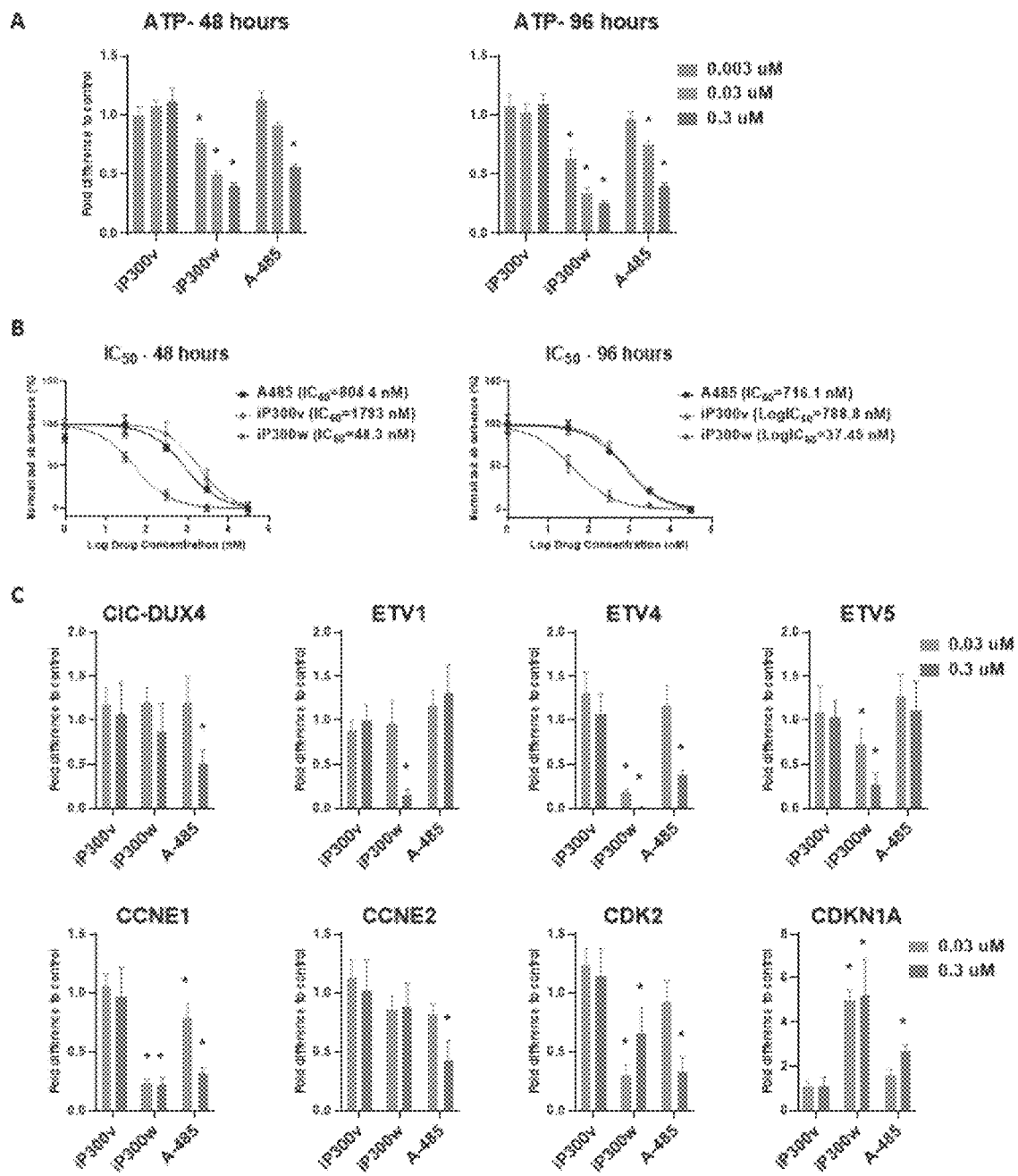
FIGS. 2A-2C. Effect of iP300w stereoisomers on CIC-DUX4 sarcoma cell line viability.
Figure 9:
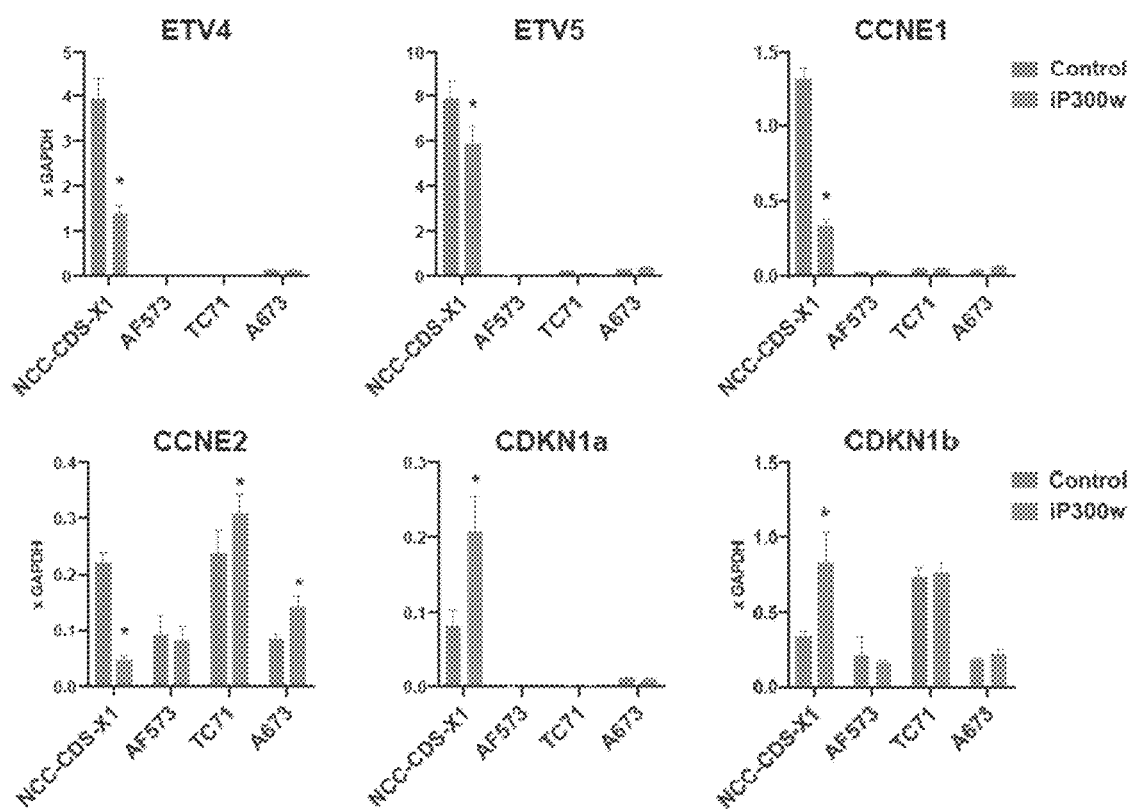
FIG. 9. RT-qPCR for CIC-DUX4 target genes in various Ewing sarcoma cell lines (AF573, TC71, A673). Cells were treated with 0.03 µM iP300w for 18 hours.

The activity of the various iP300w stereoisomers against NCC-CDS-X1 cells was evaluated. Cultures were treated with serial dilutions, ranging from 0.003 µM to 3.0 µM, for up to 96 hours. In cells treated with iP300w, a significant decrease in cell viability was evident at the lowest concentration (0.003 µM) at 48 and 96 hours (FIG. 3A). The effect was dose- and time-dependent. In addition to iP300w, two compounds, stereoisomer iP300v and related compound A-485 also showed activity, but at higher concentrations. $IC_{50}$ values were calculated: iP300v and A-485 are approximately 200-fold less potent than iP300w. (FIG. 2B and FIG. 9).

Next, the effect of the stereoisomers on the CIC-DUX4 target genes in cells cultured with the compounds for 24 hours was analyzed. Significant down-regulation of all of the direct targets, ETV1, 4, and 5, was detected, but only in the group treated with iP300w (FIG. 4B). iP300v and A-485 at the highest concentration also had a notable effect on ETV4. Taken together, based on the cell viability assay and the gene expression analyses, iP300w was identified as the most potent inhibitor of CIC-DUX4.

iP300w Inhibits CIC-DUX4 Sarcoma Cell Line Proliferation.

Figure 8:
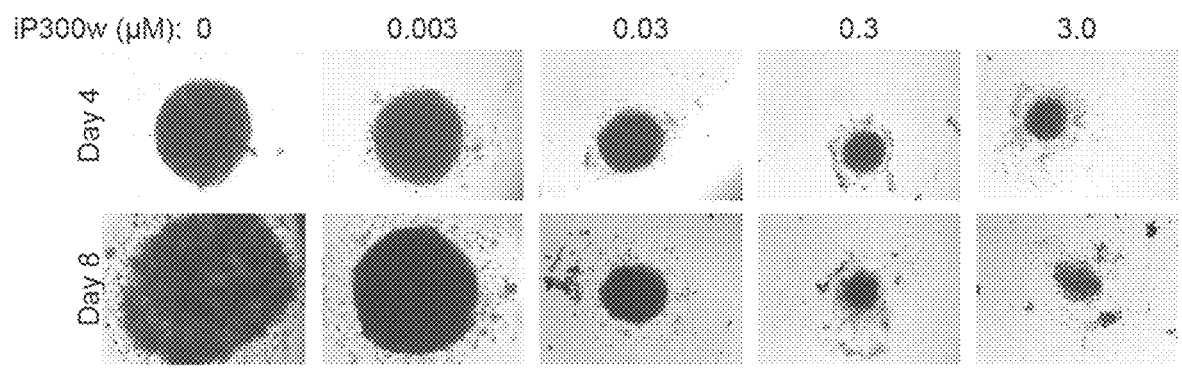
FIG. 8. Morphology of NCC-CDS-X1 spheres at day 4 and 8 of treatment with different concertation of iP300w.

To evaluate the consequences of iP300w treatment of CDS cells, its effects on both monolayer cultures as well as 3D spheres was determined in both CDS cell lines. Inhibition of proliferation was morphologically apparent as early as 24 hours after iP300w treatment and progressed with time (FIG. 2A). Using the cell viability assay, it was determined that 0.003 µM was the lowest effective concentration on day 2 in both lines (FIG. 2B). The dose and time inhibitory effect of p300w on CDS cell sphere formation and growth was also evident (FIG. 2C. FIG. 8). Two independent approaches, Ki-67 staining and EdU incorporation, revealed that iP300w treatment arrested proliferation of most cells. An almost complete absence of Ki-67 positive staining was observed in both NCC-CDS-X1 and Kitra-SRS cells at 24 (FIG. 2D) hours, and progressive reductions were obtained with EdU labeling until virtually no cells were labelled at 48 hours (FIGS. 2E and F).

CDS cells were also tested for the effects of pulses of iP300w exposure. Interestingly, a 4-hour pulse significantly reduced proliferation rate measured 20 hours later (FIGS. 2G, and H). The effect was even more dramatic in the cells treated for 24 hours; they were not able to restore the cell cycle 48 hours after the pulse (FIGS. 2G and H).

To determine whether iP300w was particularly active against CDS cells, vis-à-vis other related cancer cell lines, viability of 3 different Ewing sarcoma (ES) cell lines and several different immortalized cell lines treated with iP300w were compared. Doses of 0.003 and 0.03 µM iP300w were only effective for CIC-DUX4 driven sarcomas and not for the other cell lines (FIG. 2I). Furthermore, gene expression analyses confirmed the specificity of iP300w to CDS. In ES cell lines, iP300w did not affect the basal expression of CIC-DUX4 target genes like ETV4 and CCNE1, or cell cycle-related genes (FIG. 9).

Figures 10A, 10B, 10C:
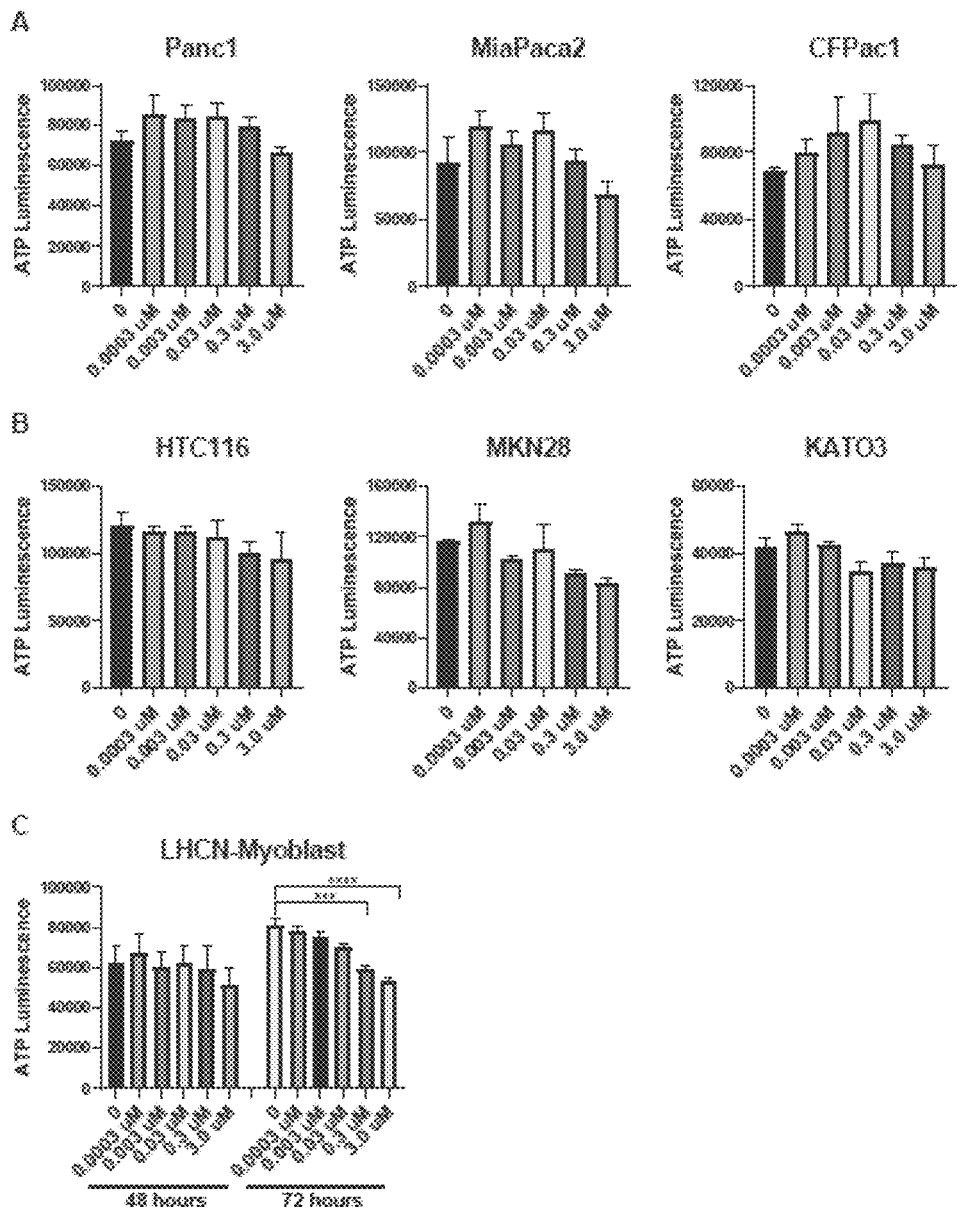
FIGS. 10A-10C. Viability assays for various cell lines exposed to iP300w.

Pancreatic and colorectal cancer cell lines were treated with iP300v to further distinguish its specificity to CDS from general cytotoxicity. p300/CBP have been correlated with the invasive and migratory properties of pancreatic and colorectal cancers (Iyer, N. G. et al., *Proceedings of the National Academy of Sciences of the United States of America* 101, 7386-7391 (2004); and Paladino, D. et al. *Oncotarget* 7, 7253-7267 (2016)). Notably, no significant effect on cell viability in the tested cell lines was observed (FIGS. 10A and B), however, a mild suppression of proliferation of iP300w at a concentration of 0.3 µM or higher after 3 days of treatment was observed (FIG. 10C). This further supports the specific efficacy of iP300w against cancers bearing p300-dependent oncogenic fusion transcription factors (such as CIC-DLUX4), vis-à-vis cancers that may show some degree of growth inhibition by iP300w due simply to p300-dependent proliferative pathways.

Finally, the effectiveness of iP300w to suppress CDS tumor growth in vivo was assessed. NCC-CDS-X1 cells were used to generate subcutaneous xenograft tumors in immunodeficient NSG mice (n=8). When tumors were palpable (day 9) iP300w injections (1.4 mg/kg b.i.d.) were initiated and the progression of tumor growth was monitored. While tumor growth was evident in the control mice, growth was halted (5/8) or significantly diminished (3/8) in the treated mice (FIG. 2 J, K).

iP300w Suppresses the CIC-DUX4 Induced Transcriptome

Next, global transcriptional profiles of NCC-CDS-X1 cells treated with iP300w were investigated. RNA-seq performed after treatment with iP300w identified 1182 down-regulated and 872 up-regulated genes 4 hours post-treatment and 2042 down-regulated and 1658 up-regulated genes 24 hours post-treatment (2-fold or greater change in gene expression (log 2FC>1 or <-1), Benjamini-Hochberg adjusted p-value <0.05, mean counts across samples >10 and FPKM in the control or iP300w-treated sample >2.5). Among these differentially expressed genes, 170 and 244 were changed by more than 10-fold at 4 hour and 24 hours, respectively (FIG. 3A).

Using the set of 165 CIC-DUX4 targets identified by Okimoto, R. A. et al., *J Clin Invest* 129, 3401-3406 (2019), numerous key transformation-regulatory genes were found, including ETV1, ETV4 and CCNE1, to be significantly downregulated within 4 hours of iP300w treatment, and the vast majority of CIC-DUX4 targets to be downregulated by 24 hours of iP300w treatment (FIG. 3B). This contrasts with the global background of gene expression changes, which were divided among upregulation and downregulation, and argues that iP300w has a predominately antagonistic effect on the genes induced by the oncogenic CIC-DUX4 transformation. Further supporting this notion is that one of the rare, upregulated genes was p21 (CDKN1A, upregulated in the 24 hours).

Figures 11A, 11B:
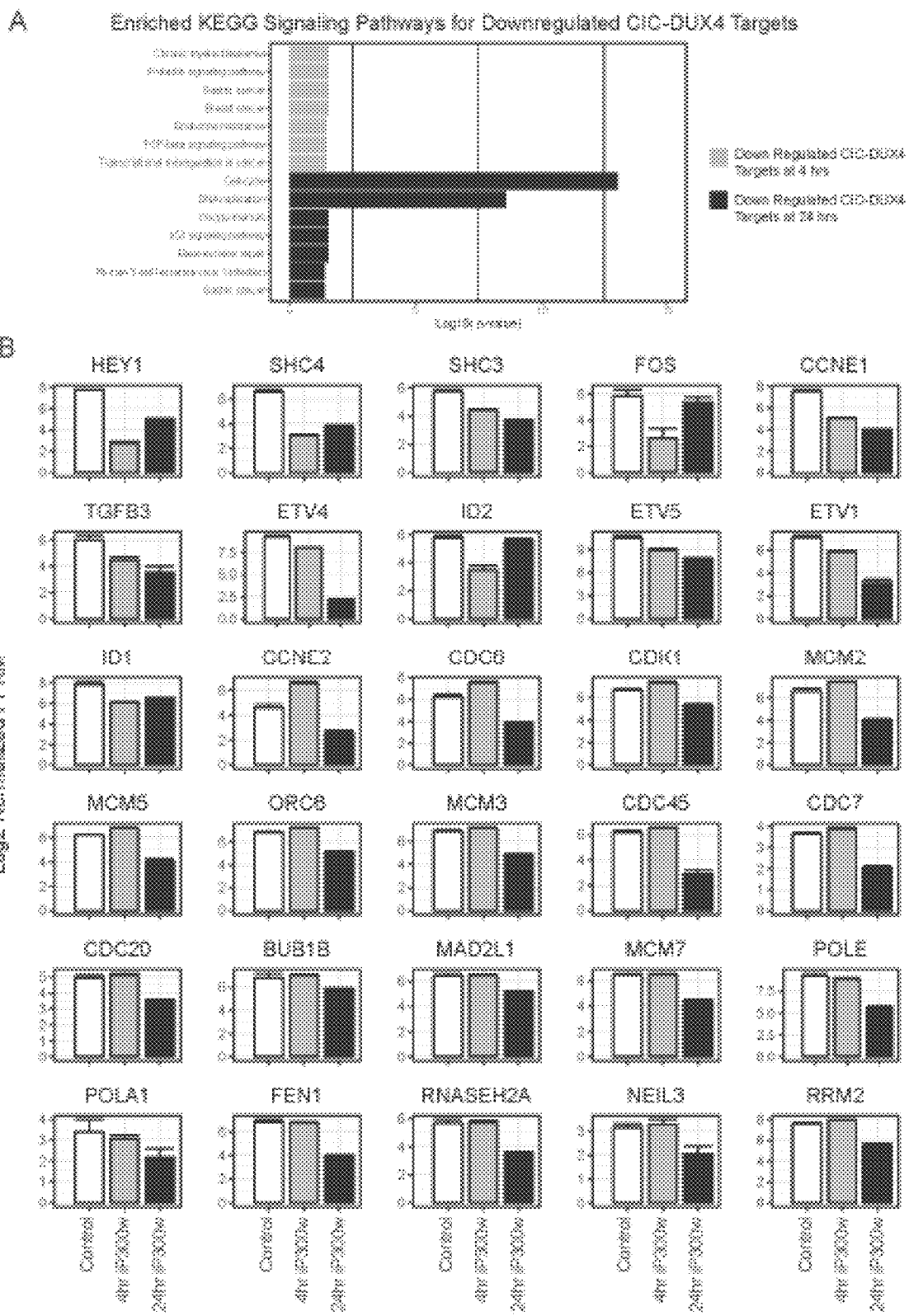
FIGS. 11A-11B. Pathway Analysis for targets of CIC-DUX4 downregulated upon treatment with iP300w.

Because iP300w treatment affected many genes not previously described as CIC-DUX4 targets, enrichment analysis was performed with Kyoto Encyclopedia of Genes and Genomes (KEGG) pathways with the up and downregulated genes (FIGS. 3C and D). Several pathways related to cancer, as well as signaling pathways frequently misregulated in cancer, were enriched among the genes downregulated at 4 hours, including the TGF-beta, WNT, and MAPK signaling pathways. By 24 hours the enriched pathways for down-regulated genes also included ribosome biogenesis, DNA replication, and cell cycle consistent with previously observed inhibition of cell cycle. A similar set of pathways was enriched among the down-regulated genes previously identified as CIC-DUX4 targets. A set of 30 iP300w responsive genes were identified among the CIC-DUX4 targets that contribute to these pathways including ETV1, ETV4, ETV5, CCNE1, and TGFB3 as central to the transformation by CIC-DUX4 that can be reversed by inhibiting p300/CBP (FIG. 11).

CIC-DUX4 Induces Global 113 Acetylation, which is Reversed by iP300w.

Figures 4A, 4B, 4C:
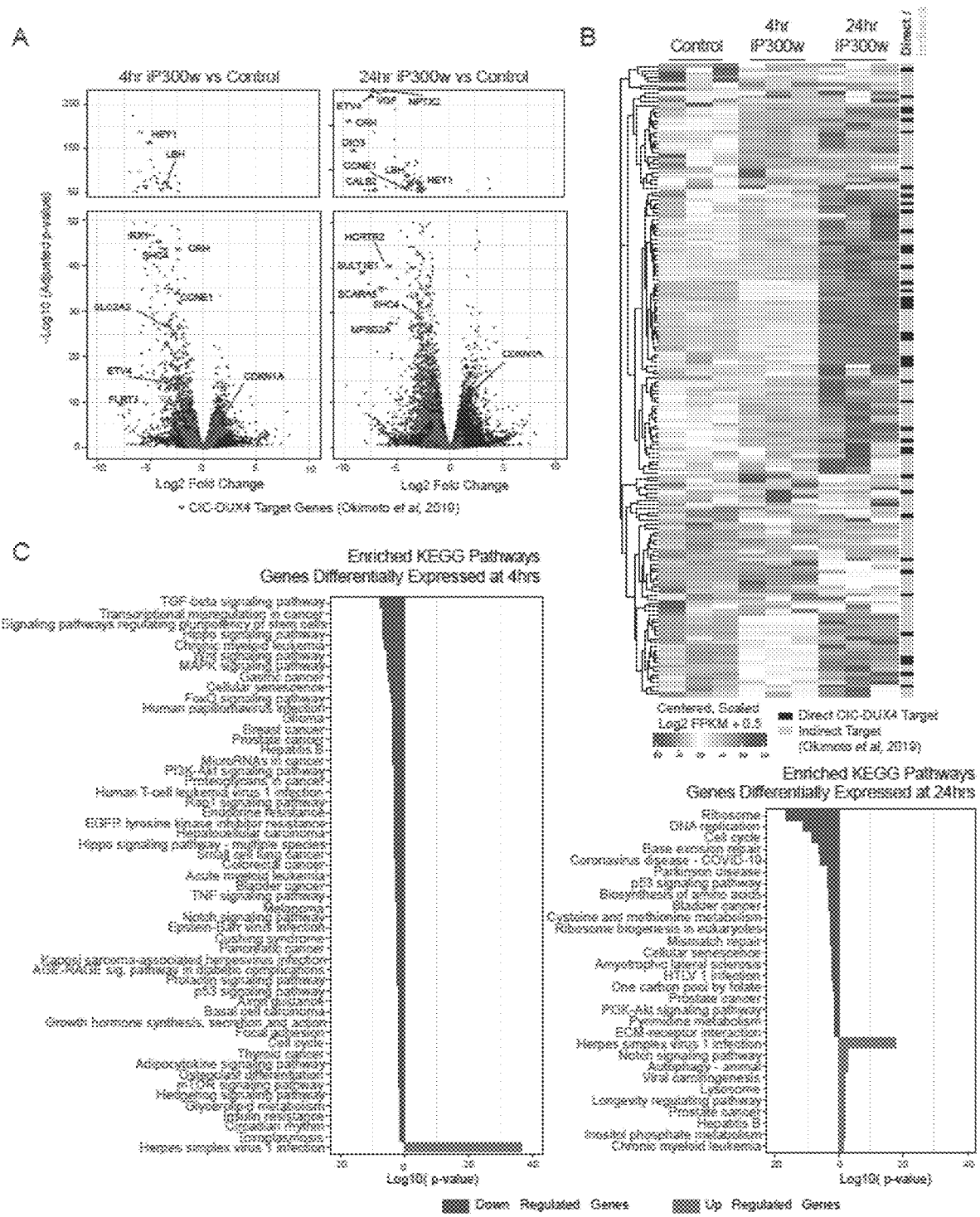
FIGS. 4A-4C. iP300w suppresses the CIC-DUX4 target transcriptome.
Figures 5A, 5B, 5C, 5D:
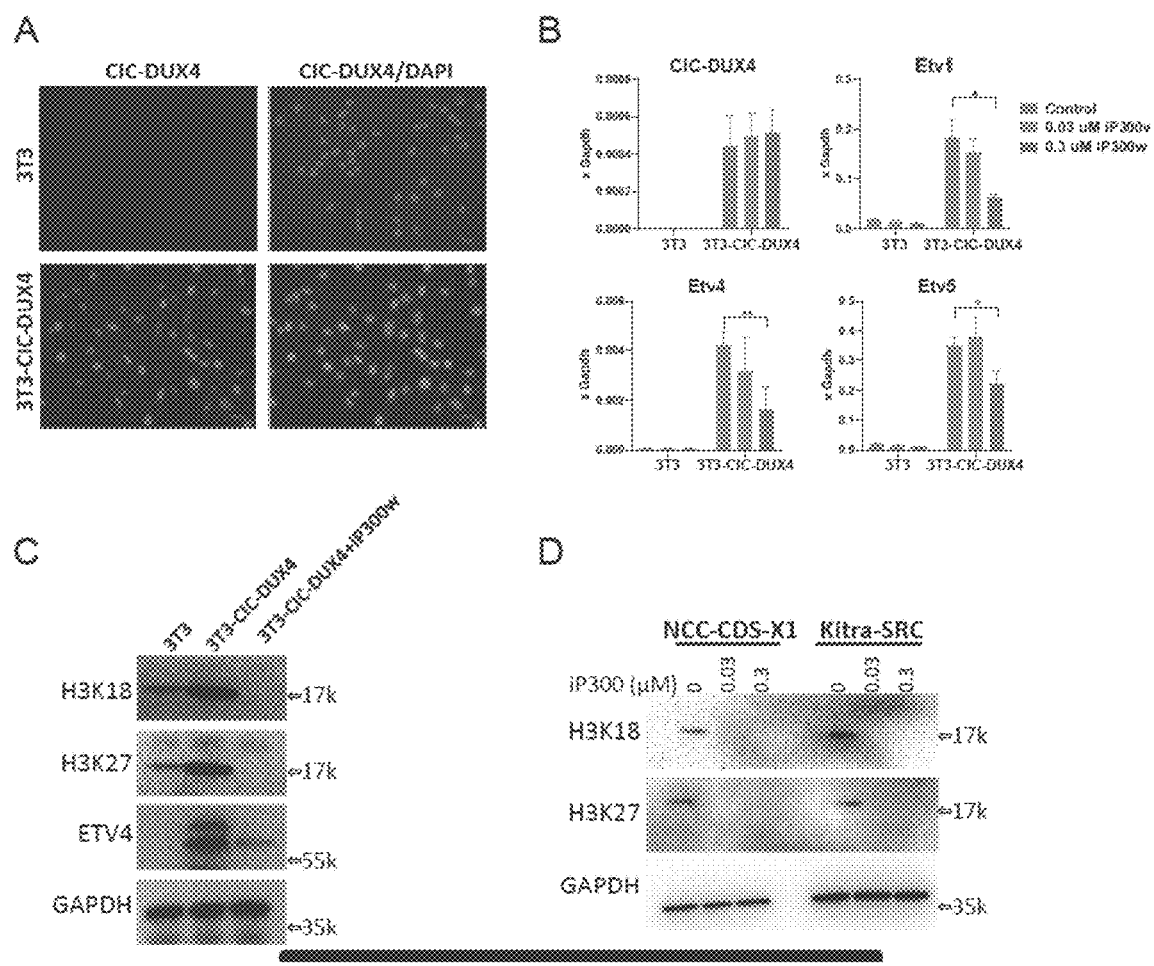
FIGS. 5A-5D. CIC-DUX4 induces H3 acetylation that is reversible by iP300w.
Figure 6:
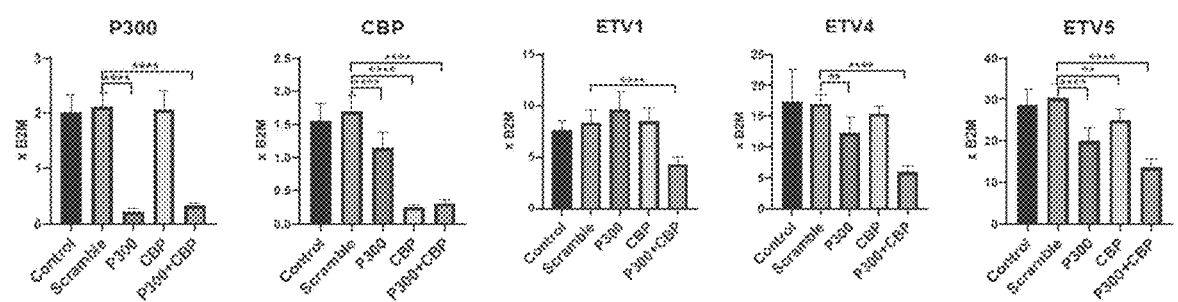
FIG. 6. RT-qPCR for CIC-DUX4 target genes in Kitra-SRC cells. RNA was harvested 48 hours post-transfection with siRNAs targeting P300 and CBP. Data are presented as mean±SEM; *p<0.05, p<0.01, *p<0.001 by one-way ANOVA. Results are presented as relative expression to B2M control (n=3).
Figures 12A, 12B, 12C:
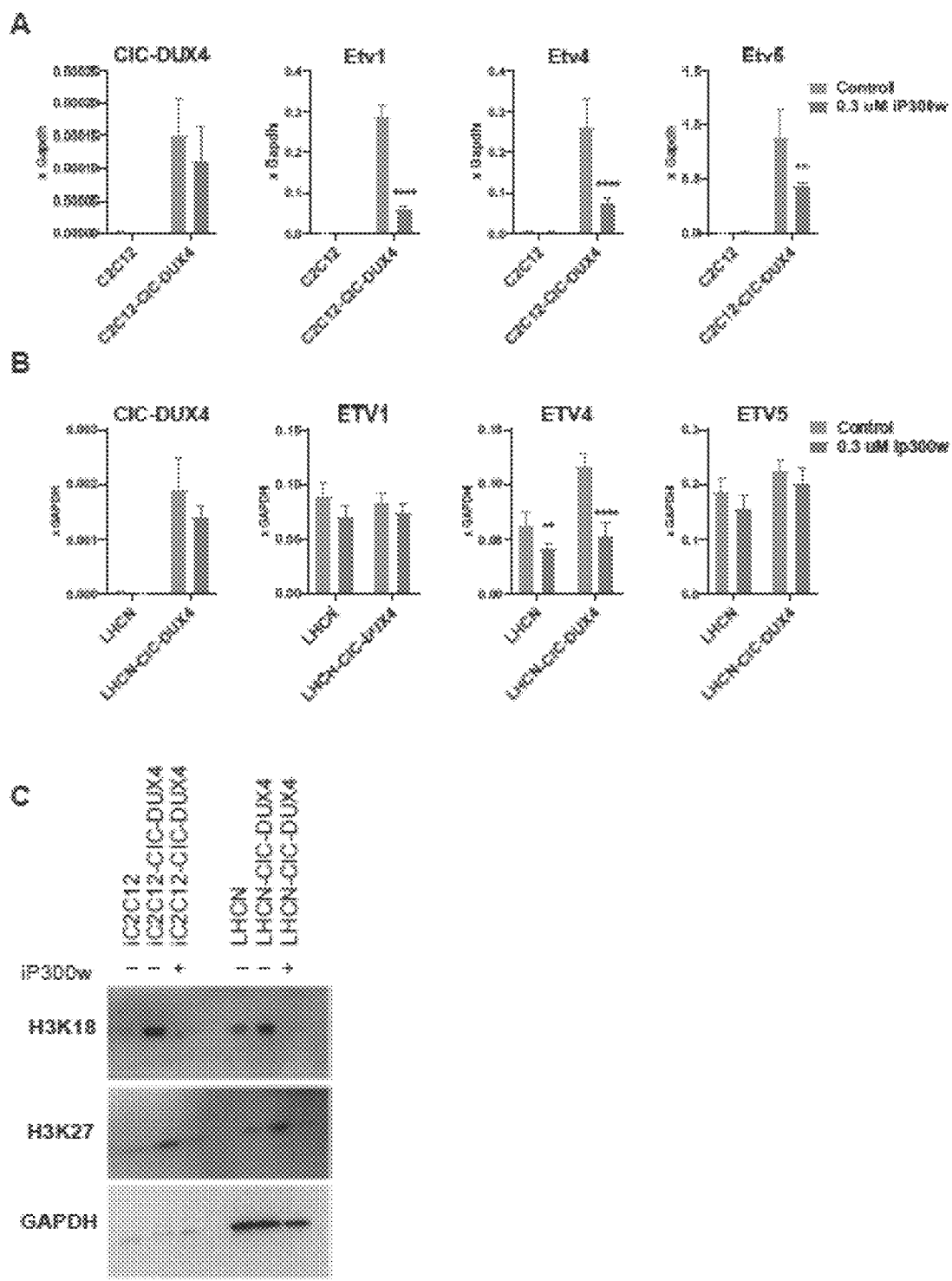
FIGS. 12A-12C. Effects of iP300w on mouse and human myoblast cell lines.

Finally, DUX4 expression is known to lead to a global increase of H3K18 and H3K27 acetylation, through a mechanism that is as yet undetermined, but dependent on p300 activity (Bosnakovski, D. et al., *Sci Adv* 5, eaaw7781 (2019)). To determine whether CIC-DUX4, which bears the p300 interaction domain of DUX4, would have this same activity, different sets of cell lines that constitutively overexpress CIC-DUX4 were generated (FIG. 4A and FIGS. 12A and 12B). Multiple cell lines, of both mouse and human origin, were used to exclude cell-type-specific effects. In each cell line, overexpression of CIC-DUX4 resulted in induction of ETV1. 4, and 5, which was reversible with iP300w treatment (FIG. 4B and FIGS. 12A and B) indicating the relevant functionality of CIC-DUX4 expressed in each line, and further demonstrating the effectiveness of iP300w to interfere with the CIC-DUX4/ETV4 transformation axis.

The global acetylation status of H3K18 and H3K27 after CIC-DUX4 induction was then investigated. It is well accepted that acetylation of both H3 lysines is facilitated by p300/CBP and that these modifications mark active enhancers (Raisner, R. et al., *Cell Rep* 24, 1722-1729 (2018); Visel, A. et al., *Nature* 457, 854-858 (2009); and Jin, Q. et al., *EMRO J* 30, 249-262 (2011)), however whether and how an increase in the global balance of acetylated to nonacetylated H3 would lead to elevated global transcription and whether this is relevant to transformation is unclear. Expression of CIC-DLUX4 resulted in dramatically increased global acetylation on both lysines in all of the analyzed cell lines (FIG. 4C, and FIG. 12C). This acetylation was dependent on p300/CBP, as it was abolished in the presence of iP300w. Importantly, it was found that iP300w reduces global H3K18 and H3K27 acetylation in NCC-CDS-X1 and Kitra-SRS CDS cell lines (FIG. 4D). Taken together, this data shows that iP300w prevents and reverses CIC-DUX4-induced H3K18 and H3K27 acetylation.

Discussion

CIC-DUX4, which bears the p300-interacting DUX4 C-terminus, activates transcription in a way that is mechanistically related to DUX4, namely, being critically dependent on p300/CBP histone acetyltransferase activity. p300 and CBP are histone acetyltransferases that regulate gene expression in a wide range of cellular processes, including proliferation, differentiation, response to DNA damage, senescence, and apoptosis. Furthermore, they interact with multiple oncogenes/tumor suppressors and are essential for their activity and carcinogenesis. It has been found that the oncogenic mechanism of CIC-DUX4, which involves both deregulation of cell cycle through upregulation of genes such as CCE1 as well as induction of invasion and metastasis potential through upregulation of ETV4 and related Ets-family genes, is critically dependent on p300/CBP. Knockdown of both histone acetyltransferases p300 and CBP in CDS cell lines results in the prevention of CIC-DUX4 target gene expression leading to cell cycle arrest. Thus, disruption of the CIC-DUX4/p300/CBP axis is a potential druggable approach for CDS treatment.

Currently, there are four different established CDS cell lines, NCC-CDS-X1 and NCC-CDS-X3 which originate from the same patient, NCC-CDS2-C1, and Kitra-SRS (Nakai, S. et al., *Scientific reports* 9, 15812 (2019); Oyama, R. et al., *Scientific reports* 7, 4712 (2017); and Yoshimatsu, Y. et al., *Hum Cell* 33, 427-436 (2020)). All have been used in multiple screens with known FDA-approved anticancer molecules. Only a handful of drugs, that are not DNA intercalators, like ponatinib, crizotinib, and bortezomib, have shown some degree of effectiveness in vitro (Nakai, S. et al., *Scientific reports* 9, 15812 (2019); Oyama, R. et al, *Scientific reports* 7, 4712 (2017); and Yoshimatsu, Y. et al., *Hum Cell* 33, 427-436 (2020)). By investigating downstream transcriptional targets of CIC-DUX4, Okimoto, R. A. et al., *J Clin Invest* 129, 3401-3406 (2019 identified the CCNE-CDK2 complex as a potential CDS druggable target. Using dinacibil, an approved CDK2 inhibitor, they were able to suppress tumor growth and metastasis in a mouse xenograft model.

Applying a similar molecular approach, Nakai. S. et al., *Scientific reports* 9, 15812 (2019) found that the viability of Kitra-SRS cells depends on the IGF1/IGF1R pathway, which if it is interrupted with linsitinib, an IGF-1R inhibitor, results in reduced cell proliferation. Both approaches deserve consideration in developing specific therapies for CDS even though they are focused on distant indirect CIC-DUX4 targets. The optimal therapy for CDS would be inactivation of CIC-DUX4, either directly or through targeting of its essential coactivators. Thus, specific inhibition of p300/CBP represents a rationally targeted pharmacological approach to the treatment of CDS.

A-485 was shown to suppress proliferation of a wide spectrum of cancer cell lines, more prominently in those of hematopoietic origin (Lasko, L. M. et al., *Nature* 550, 128-132 (2017)). A-485 has also been found to be effective against high MITF-expressing melanoma cell lines and nuclear protein of the testis (NUT) midline carcinoma (Wang, R. et al., *Mol Cancer Ther* 17, 2543-2550 (2018); and Zhang, X. et al., *Oncogene* 39, 4770-4779 (2020)). Additionally, A-485 increases the sensitivity of non-small-cell lung carcinoma cells to TRAIL, or A-485 in combination with PD-L1 blockade treatment dramatically reduced prostate cancer tumor growth (Zhang, B., et al., *Biochem Pharmacol* 175, 113914 (2020); and Liu, J. et al., *Oncogene* 39, 3939-3951 (2020). While the general efficacy of A-485 against various tumor cell lines is interesting, none of the lines tested involved CIC-DUX4 fusions. Furthermore, doses used in these studies are relatively high. Notably, in studies screening FDA approved drugs on CDS cells, screening was performed at 10 µM, while in the studies herein, iP300w is effective at 0.003 µM.

In testing against cancer and colorectal cell lines expected to have a general p300/CBP dependence, growth inhibition was not observed until concentrations of 0.3 µM and above, highlighting the extreme sensitivity of CIC-DUX4-induced cancers to iP300w. Furthermore, iP300w was about two orders of magnitude more active than A-485 in the cell-based assays. Considering that these compounds begin to show toxic effects on cells at micromolar concentrations, retaining activity down into the low sub-micromolar range will be essential, making A-485 undesirable. The greater potency of iP300w is thus critical. Indeed, the lack of toxicity at the effective concentration is highlighted by the fact that the use of iP300w was against full length DUX4, a toxic protein that causes cell death, and this cell death was prevented by iP300w (Bosnakovski, D. et al., *Sci Adv* 5, eaaw7781 (2019)).

As current therapies for CDS are ineffective or very short-lived, with tumors rapidly developing resistance, the ability to inhibit the molecular driver of the disease could provide a transformative therapy for these patients. Based on the in vitro and in vivo data presented here, iP300w is a very promising candidate for targeted therapy in CDS. Furthermore, the extreme sensitivity of CDS cell lines to iP300w vis-à-vis other cancer lines highlights the value of specifically targeting the oncogenic driver. It is likely that certain other oncogenic fusion transcription factors carry a similar p300/CBP-dependence, and where this occurs, iP300w might be similarly effective. Thus, the continued translational development of iP300w for cancer and CDS in particular is strongly warranted.

All publications, patents, and patent documents (including Bosnakovski D. et al., *Oncogenesis* 10, 68 (2021); https://doi.org/10.1038/s41389-021-00357-4) are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A method for treating a pediatric sarcoma involving one or more translocations generating an oncogenic fusion transcription factor that requires p300/CBP for activity in a human, comprising administering a compound of formula (I):

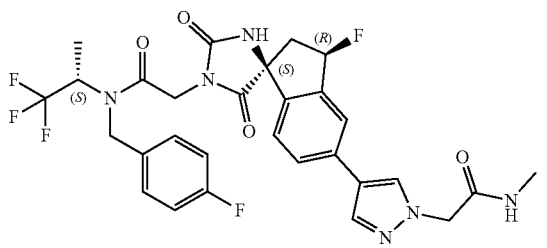

or a pharmaceutically acceptable salt thereof to the human.

2. The method of claim 1, wherein the pediatric sarcoma involves a translocation involving DUX4.

3. The method of claim 1, wherein the pediatric sarcoma involves CIC-DUX4 fusion.

4. The method of claim 1, wherein the pediatric sarcoma is a sarcoma that involves CIC-DUX4 fusion.

5. A pharmaceutical composition comprising compound of formula (I):

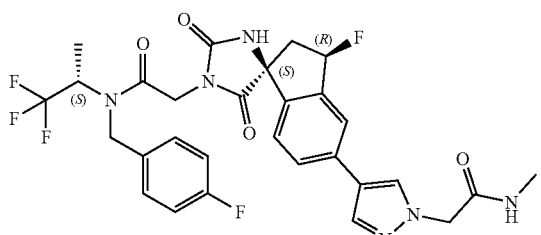

or a pharmaceutically acceptable salt thereof and a second therapeutic agent useful for treating a cancer involving one or more translocations generating an oncogenic fusion transcription factor that requires p300/CBP for activity.

* * * * *